United States Patent
Matsumoto et al.

(10) Patent No.: US 8,932,845 B2
(45) Date of Patent: Jan. 13, 2015

(54) HIGHLY PRODUCTIVE ISOPROPYL ALCOHOL-PRODUCING BACTERIUM

(75) Inventors: Yoshiko Matsumoto, Mobara (JP); Junichiro Hirano, Tokyo (JP); Takashi Morishige, Chiba (JP); Tomokazu Shirai, Yokohama (JP); Hitoshi Takahashi, Chiba (JP); Koh Amano, Mobara (JP); Nozomi Takebayashi, Mobara (JP); Mitsufumi Wada, Chiba (JP); Hiroshi Shimizu, Ibaraki (JP); Chikara Furusawa, Ibaraki (JP); Takashi Hirasawa, Minoh (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 13/583,184

(22) PCT Filed: Mar. 4, 2011

(86) PCT No.: PCT/JP2011/055142
§ 371 (c)(1),
(2), (4) Date: Sep. 6, 2012

(87) PCT Pub. No.: WO2011/111638
PCT Pub. Date: Sep. 15, 2011

(65) Prior Publication Data
US 2013/0005008 A1    Jan. 3, 2013

(30) Foreign Application Priority Data
Mar. 9, 2010    (JP) .................................. 2010-052249

(51) Int. Cl.
| | |
|---|---|
| *C12N 1/20* | (2006.01) |
| *C12N 9/00* | (2006.01) |
| *C12P 7/04* | (2006.01) |
| *C07H 21/04* | (2006.01) |
| *C12N 9/04* | (2006.01) |
| *C12N 9/02* | (2006.01) |
| *C12N 9/10* | (2006.01) |
| *C12N 15/70* | (2006.01) |

(52) U.S. Cl.
CPC ................ *C12P 7/04* (2013.01); *C12N 9/0006* (2013.01); *C12N 9/0036* (2013.01); *C12N 9/1029* (2013.01); *C12N 15/70* (2013.01)
USPC ................... 435/252.33; 435/252.3; 435/157; 435/183; 536/23.2

(58) Field of Classification Search
CPC ............ C12P 7/04; C12P 41/002; C12P 7/02; C12P 7/065; C12P 2203/00; C12N 15/52; C12N 9/0008; C12N 15/74; C12N 9/10; C12N 1/20; C12N 15/70; C12N 9/0036; C12Y 401/01004; C12Y 101/0108; C12Y 203/01009; C12R 1/01
See application file for complete search history.

(56) References Cited

U.S. PATENT DOCUMENTS

| | | | |
|---|---|---|---|
| 2008/0145904 A1* | 6/2008 | Groger et al. .................. 435/157 |
| 2010/0203604 A1 | 8/2010 | Yukawa et al. | |
| 2010/0221800 A1 | 9/2010 | Liao et al. | |
| 2010/0311135 A1 | 12/2010 | Takebayashi et al. | |

FOREIGN PATENT DOCUMENTS

| | | |
|---|---|---|
| CN | 101027403 A | 8/2007 |
| EP | 2 006 386 A1 | 12/2008 |
| JP | 2008-507989 A | 3/2008 |
| JP | 2009-247217 A | 10/2009 |
| WO | WO-2008/131286 A1 | 10/2008 |
| WO | WO 2009/008377 | 1/2009 |
| WO | WO 2009/012210 A2 | 1/2009 |
| WO | WO 2009/023493 A1 | 2/2009 |
| WO | WO 2009/028582 A1 | 3/2009 |
| WO | WO 2009/049274 A2 | 4/2009 |
| WO | WO-2009/078973 A2 | 6/2009 |
| WO | WO 2009/103026 A1 | 8/2009 |
| WO | WO 2009/111672 A1 | 9/2009 |
| WO | WO 2011/031897 A1 | 3/2011 |

OTHER PUBLICATIONS

Nissen et al. Expression of a cytoplasmic transhydrogenase in *Saccharomyces cerevisiae* results in formation of 2-oxoglutarate due to depletion of NADPH pool, Yeast (2001), 18:19-32.*
Extended European Search Report in corresponding EP Application No. 11753297.8, dated Sep. 24, 2013.
International Search Report PCT/JP2011/055142 dated Jun. 7, 2011.
T. Hanai et al., "Engineered Synthetic Pathway for Isopropanol Production in *Escherichia coli*", Applied and Environmental Microbiology, Dec. 2007, vol. 73, No. 24, pp. 7814-7818.
Toru Jojima et al., "Production of isopropanol by metabolically engineered *Escherichia coli*", Appl. Microbiol. Biotechnol. (2008) 77: 1219-1224.
A. Weckbecker et al., "Improved synthesis of chiral alcohols with *Escherichia coli* cells co-expressing pyridine nucleotide transhydrogenase,. $NADP^+$—dependent alcohol dehydrogenase and $NAD^+$—dependent formate dehydrogenase" Biotechnology Letters 2004, vol. 26, No. 22, pp. 1739-1744.
J.W. Chin et al., "Analysis of NADPH Supply During Xylitol Production by Engineered *Escherichia coli*" Biotechnology and Bioengineering Jan. 1, 2009, vol. 102, No. 1, pp. 209-220.
Japanese Office Action dated Feb. 4, 2014 issued in Japanese Application No. 2012-504437 (w/English translation).
Chinese Office Action dated Apr. 3, 2014 issued in Application No. 201180012535.5 (with partial English translation).

* cited by examiner

*Primary Examiner* — Iqbal H Chowdhury
(74) *Attorney, Agent, or Firm* — Foley & Lardner LLP

(57) ABSTRACT

An isopropyl alcohol-producing *Escherichia coli* equipped with an isopropyl alcohol production system, having at least one enhanced enzyme activity selected from the group consisting of an enhanced malate dehydrogenase activity, an enhanced $NAD(P)^+$ transhydrogenase (AB-specific) activity, and an enhanced thiolase activity, and an isopropyl alcohol producing method including producing isopropyl alcohol from a plant-derived raw material using the isopropyl alcohol-producing *Escherichia coli*.

13 Claims, 1 Drawing Sheet

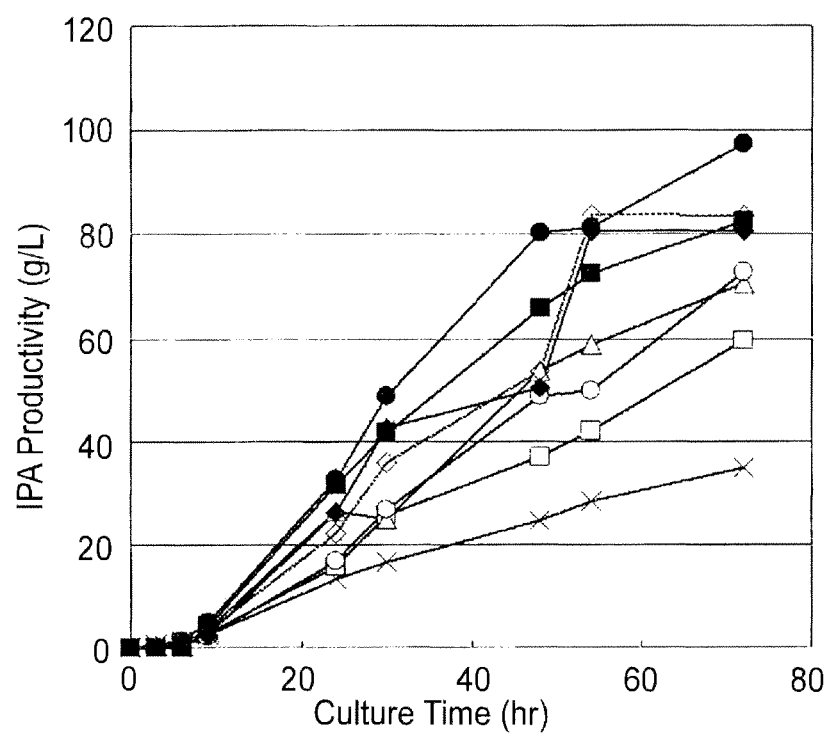

SEQUENCE LISTING

<160> NUMBER OF SEQ ID NOS: 20

<210> SEQ ID NO 1
<211> LENGTH: 30
<212> TYPE: DNA
<213> ORGANISM: Artificial

```
<220> FEATURE:
<223> OTHER INFORMATION: primer

<400> SEQUENCE: 1
cgctcaattg caatgattga cacgattccg                                          30

<210> SEQ ID NO 2
<211> LENGTH: 32
<212> TYPE: DNA
<213> ORGANISM: Artificial
<220> FEATURE:
<223> OTHER INFORMATION: primer

<400> SEQUENCE: 2
acagaattcg ctatttgtta gtgaataaaa gg                                       32

<210> SEQ ID NO 3
<211> LENGTH: 42
<212> TYPE: DNA
<213> ORGANISM: Artificial
<220> FEATURE:
<223> OTHER INFORMATION: primer

<400> SEQUENCE: 3
gcagcaattg ctggtggaac atatgcgaat tggcatacca ag                            42

<210> SEQ ID NO 4
<211> LENGTH: 33
<212> TYPE: DNA
<213> ORGANISM: Artificial
<220> FEATURE:
<223> OTHER INFORMATION: primer

<400> SEQUENCE: 4
ggacaagctt aatttttgcg gaacattttc agc                                      33

<210> SEQ ID NO 5
<211> LENGTH: 27
<212> TYPE: DNA
<213> ORGANISM: Artificial
<220> FEATURE:
<223> OTHER INFORMATION: primer

<400> SEQUENCE: 5
atggtaccgc agtaatacgc tggttgc                                             27

<210> SEQ ID NO 6
<211> LENGTH: 33
<212> TYPE: DNA
<213> ORGANISM: Artificial
<220> FEATURE:
<223> OTHER INFORMATION: primer

<400> SEQUENCE: 6
cctctagact tccatcggtt ttattgatga tgg                                      33

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
ggtctagagc aatgattgac acgattccg                                           29
```

```
<210> SEQ ID NO 8
<211> LENGTH: 50
<212> TYPE: DNA
<213> ORGANISM: Artificial
<220> FEATURE:
<223> OTHER INFORMATION: primer

<400> SEQUENCE: 8
cgaattcgct ggtggaacat atgaaaacaa aattgatgac attacaagac        50

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
gcggtacctt atttgctctc ctgtgaaacg                              30

<210> SEQ ID NO 10
<211> LENGTH: 31
<212> TYPE: DNA
<213> ORGANISM: Artificial
<220> FEATURE:
<223> OTHER INFORMATION: primer

<400> SEQUENCE: 10
gctctagatg ctgaaatcca ctagtcttgt c                            31

<210> SEQ ID NO 11
<211> LENGTH: 29
<212> TYPE: DNA
<213> ORGANISM: Artificial
<220> FEATURE:
<223> OTHER INFORMATION: primer

<400> SEQUENCE: 11
tactgcagcg ttccagcacc ttatcaacc                               29

<210> SEQ ID NO 12
<211> LENGTH: 29
<212> TYPE: DNA
<213> ORGANISM: Artificial
<220> FEATURE:
<223> OTHER INFORMATION: primer

<400> SEQUENCE: 12
ggtctagagc aatgattgac acgattccg                               29

<210> SEQ ID NO 13
<211> LENGTH: 45
<212> TYPE: DNA
<213> ORGANISM: Artificial
<220> FEATURE:
<223> OTHER INFORMATION: primer

<400> SEQUENCE: 13
aatatgcatg ctggtggaac atatgaaagg ttttgcaatg ctagg             45

<210> SEQ ID NO 14
<211> LENGTH: 44
<212> TYPE: DNA
<213> ORGANISM: Artificial
<220> FEATURE:
<223> OTHER INFORMATION: primer
```

<400> SEQUENCE: 14
gcggatccct cgagttataa tataactact gctttaatta agtc         44

<210> SEQ ID NO 15
<211> LENGTH: 54
<212> TYPE: DNA
<213> ORGANISM: Artificial
<220> FEATURE:
<223> OTHER INFORMATION: primer

<400> SEQUENCE: 15
cactcgaggc tggtggaaca tatgttaaag gatgaagtaa ttaaacaaat tagc    54

<210> SEQ ID NO 16
<211> LENGTH: 61
<212> TYPE: DNA
<213> ORGANISM: Artificial
<220> FEATURE:
<223> OTHER INFORMATION: primer

<400> SEQUENCE: 16
ggaattcggt accgtcgact ctagaggatc cttacttaag ataatcatat ataacttcag    60
c                                                                   61

<210> SEQ ID NO 17
<211> LENGTH: 29
<212> TYPE: DNA
<213> ORGANISM: Artificial
<220> FEATURE:
<223> OTHER INFORMATION: primer

<400> SEQUENCE: 17
cgggatcctt aattcaaccg ttcaatcac              29

<210> SEQ ID NO 18
<211> LENGTH: 27
<212> TYPE: DNA
<213> ORGANISM: Artificial
<220> FEATURE:
<223> OTHER INFORMATION: primer

<400> SEQUENCE: 18
ttccatatga aaaattgtgt catcgtc                27

<210> SEQ ID NO 19
<211> LENGTH: 44
<212> TYPE: DNA
<213> ORGANISM: Artificial
<220> FEATURE:
<223> OTHER INFORMATION: primer

<400> SEQUENCE: 19
cgggatcccg gagaaagtca tatggatgac cagttaaaac aaag         44

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
gctctagatt acagcggttg ggtttgcgc              29

HIGHLY PRODUCTIVE ISOPROPYL ALCOHOL-PRODUCING BACTERIUM

TECHNICAL FIELD

The present invention relates to an isopropyl alcohol-producing bacterium and an isopropyl alcohol producing method using the same.

BACKGROUND ART

Propylene is an important basic raw material of synthetic resins such as polypropylene and petrochemical products and used in a wide variety of products such as automobile bumpers, food containers, films, and medical instruments.

Isopropyl alcohol produced from a plant-derived raw material can be converted to propylene through a dehydration process. Therefore, isopropyl alcohol is promising as a raw material for carbon-neutral propylene. At present, Kyoto Protocol mandates that developed countries as a whole reduce carbon dioxide emissions by 5% as compared to 1990 levels in the 2008 to 2012 period. Therefore, carbon-neutral propylene is extremely important in the global environment because of its versatility.

Bacteria that assimilate a plant-derived raw material to produce isopropyl alcohol are already known. For example, the pamphlet of WO2009/008377 discloses a bacterium modified to produce isopropyl alcohol from glucose as a raw material and described that the bacterium has excellent properties as a biocatalyst for industrial production because of its high selectivity of isopropyl alcohol.

In an isopropyl alcohol-producing *Escherichia coli*, since the raw material for isopropyl alcohol is glucose, a large number of compounds obtained by glycolysis and catabolism can all be by-products. On the other hand, since those compounds may be substances essential for growth of *Escherichia coli*, it is impossible to completely suppress the amount of glucose consumed by those secondary reactions. Accordingly, to increase the production rate of isopropyl alcohol while minimizing by-products, it is necessary to maximize metabolic flow to isopropyl alcohol while considering all metabolic reactions occurring in *Escherichia coli*, and various techniques have been proposed from the viewpoint of biological activity and substance production.

For example, the pamphlet of WO2009/008377 discloses an isopropyl alcohol-producing bacterium in which respective genes of acetoacetate decarboxylase, isopropyl alcohol dehydrogenase, CoA transferase, and thiolase are introduced to allow isopropyl alcohol to be produced from a plant-derived raw material. It is described that the isopropyl alcohol-producing bacterium can achieve a production rate of 0.6 g/L/hr and an amount of accumulation of 28.4 g/L.

The pamphlet of WO2009/049274 and *Appl. Environ. Biotechnol.*, 73(24), pp. 7814-7818, (2007) disclose *Escherichia coli* in which respective genes of acetyl-CoA acetyltransferase, acetoacetyl CoA transferase, acetoacetate decarboxylase, and secondary alcohol dehydrogenase are introduced to produce isopropyl alcohol. It is described that those bacteria can achieve a production rate of 0.4 g/L/hr, a yield of 43.5%, and an amount of accumulation of 4.9 g/L.

The pamphlet of WO2009/028582 discloses *Escherichia coli* in which respective genes of acetoacetate carboxylase, isopropyl alcohol dehydrogenase, acetyl-CoA:acetate CoA-transferase, and acetyl-CoA acetyl transferase are introduced to produce isopropyl alcohol. It is described that the bacterium can achieve an amount of accumulation of 9.7 g/L.

*Appl. Microbial. Biotechnol.*, 77(6), pp. 1219-1224, (2008) discloses *Escherichia coli* in which respective genes of thiolase, CoA-transferase, acetoacetate decarboxylase, and primary-secondary alcohol dehydrogenase are introduced to produce isopropyl alcohol. It is described that the bacterium can achieve a production rate of 0.6 g/L/hr, a yield of 51%, and an amount of accumulation of 13.6 g/L.

The pamphlet of WO2009/103026 discloses *Escherichia coli* in which respective genes of acetoacetate decarboxylase, acetyl-CoA:acetate CoA transferase, acetyl-CoA acetyl transferase, and isopropyl alcohol dehydrogenase are introduced to allow the production of isopropyl alcohol. It is described that the bacterium is expected to have the ability to achieve a yield of 50%, a production rate of 0.4 g/L/hr, and an ultimate production of 14 g/L.

The pamphlet of WO2009/247217 discloses *Escherichia coli* in which respective genes of acetoacetate decarboxylase, CoA transferase, thiolase, and 2-propyl alcohol dehydrogenase are introduced to allow the production of isopropyl alcohol. It is described that the bacterium can achieve an ultimate production of 2 g/L.

Here, isopropyl alcohol dehydrogenase, secondary alcohol dehydrogenase, primary-secondary alcohol dehydrogenase, and 2-propyl alcohol dehydrogenase are enzymes that have different names but catalyze the same reaction. CoA transferase, acetoacetyl CoA transferase, acetyl CoA:acetate CoA transferase, and CoA-transferase are enzymes that have different names but catalyze the same reaction. In addition, acetoacetate decarboxylase and acetoacetate decarboxylase are enzymes that have different names but catalyze the same reaction, and thiolase and acetyl CoA acetyl transferase are enzymes that have different names but catalyze the same reaction. Accordingly, although the productivity of the isopropyl alcohol-producing *Escherichia coli* of the above-described documents varies, the enzymes used to produce isopropyl alcohol are equivalent to the four enzymes— acetoacetate decarboxylase, isopropyl alcohol dehydrogenase, CoA transferase, and thiolase—described in the pamphlet of WO2009/008377. For purposes such as improvement of productivity and yield, the four enzymes have been conventionally studied.

On the other hand, a method of deleting an enzyme malate dehydrogenase that a microorganism possesses is known as a method for improving the yield and productivity in substance production by the microorganism.

For example, the pamphlet of WO2009/023493 describes that, in the production of 1,4-butanediol by *Escherichia coli*, the yield is increased by disruption of a malate dehydrogenase gene that the *Escherichia coli* possesses or by simultaneous disruption of a malate dehydrogenase gene and a transhydrogenase gene that the *Escherichia coli* possesses.

Additionally, the pamphlet of WO2009/012210 describes that, in the production of ethanol by *Escherichia coli*, the yield is increased by simultaneously disrupting a malate dehydrogenase gene and a D-lactate dehydrogenase gene that the *Escherichia coli* possesses.

Furthermore, the pamphlet of WO2009/111672 describes that, in the production of dodecanol by yeast, productivity is effectively improved by simultaneously disrupting acetaldehyde-CoA dehydrogenase gene, a D-lactate dehydrogenase gene, and a malate dehydrogenase gene that the yeast possesses.

SUMMARY OF INVENTION

Problem to be Solved by Invention

However, any of the above-described bacteria capable of producing isopropyl alcohol is not considered to have sufficient production ability. Thus, a major problem to be solved has been how to improve the yield and rate of the production of isopropyl alcohol by an isopropyl alcohol-producing bacterium.

It is an object of the present invention to provide an *Escherichia coli* capable of producing isopropyl alcohol at high rate and with high yield and an isopropyl alcohol producing method using the *Escherichia coli*.

Means for Solving the Problem

The present invention has been accomplished in view of the above-described circumstances, and an isopropyl alcohol-producing *Escherichia coli* of the present invention and an isopropyl alcohol producing method of the present invention are as follows:

[1] An isopropyl alcohol-producing *Escherichia coli* equipped with an isopropyl alcohol production system, having at least one enhanced enzyme activity selected from the group consisting of an enhanced malate dehydrogenase activity, an enhanced NAD(P)$^+$ transhydrogenase (AB-specific) activity, and an enhanced thiolase activity.

[2] The isopropyl alcohol-producing *Escherichia coli* according to [1], wherein the enhanced enzyme activity includes the enhanced malate dehydrogenase activity.

[3] The isopropyl alcohol-producing *Escherichia coli* according to [1], wherein the enhanced enzyme activity includes the enhanced malate dehydrogenase activity and the enhanced thiolase activity.

[4] The isopropyl alcohol-producing *Escherichia coli* according to [1], wherein the enhanced enzyme activity includes the enhanced malate dehydrogenase activity and the enhanced NAD(P)$^+$ transhydrogenase (AB-specific) activity.

[5] The isopropyl alcohol-producing *Escherichia coli* according to [1], wherein the enhanced enzyme activity includes the enhanced malate dehydrogenase activity, the enhanced NAD(P)$^+$ transhydrogenase (AB-specific) activity, and the enhanced thiolase activity.

[6] The isopropyl alcohol-producing *Escherichia coli* according to any one of [1] to [5], wherein the enhanced enzyme activity is derived from at least one of enhancement by an enzyme gene introduced from outside a cell of the *Escherichia coli* and enhancement by enhanced expression of an enzyme gene in the cell of the *Escherichia coli*.

[7] The isopropyl alcohol-producing *Escherichia coli* according to any one of [1] to [6], wherein the enhanced enzyme activity is derived from at least one of enhancement in the genome of a host *Escherichia coli* and enhancement by plasmid introduction.

[8] The isopropyl alcohol-producing *Escherichia coli* according to any one of [1] to [7], wherein the enhanced enzyme activity is derived from a gene or genes derived from a bacterium or bacteria of the genus *Escherichia* and encoding the enzyme or enzymes.

[9] The isopropyl alcohol-producing *Escherichia coli* according to any one of [1] to [8], wherein the isopropyl alcohol production system is constructed by respective genes of acetoacetate decarboxylase, isopropyl alcohol dehydrogenase, CoA transferase, and thiolase.

[10] The isopropyl alcohol-producing *Escherichia coli* according to any one of [1] to [8], wherein the isopropyl alcohol production system is constructed by respective enzyme genes of the acetoacetate decarboxylase, the isopropyl alcohol dehydrogenase, the CoA transferase, and the thiolase, and each of the enzyme genes is independently derived from at least one prokaryote selected from the group consisting of a bacterium of the genus *Clostridium*, a bacterium of the genus *Bacillus*, and a bacterium of the genus *Escherichia*.

[11] The isopropyl alcohol-producing *Escherichia coli* according to any one of [1] to [8], wherein the acetoacetate decarboxylase activity is derived from a gene that is derived from *Clostridium acetobutylicum* and encodes the enzyme; the isopropyl alcohol dehydrogenase activity is derived from a gene that is derived from *Clostridium beijerinckii* and encodes the enzyme; and the CoA transferase activity, the thiolase activity, the malate dehydrogenase activity, and the NAD(P)$^+$ transhydrogenase (AB-specific) activity are derived from genes that are derived from *Escherichia coli* and encode the respective enzymes.

[12] An isopropyl alcohol producing method including producing isopropyl alcohol from a plant-derived raw material using the isopropyl alcohol-producing *Escherichia coli* according to any one of [1] to [11].

BRIEF DESCRIPTION OF DRAWINGS

FIG. 1 is a graph comparing IPA-producing abilities of various kinds of IPA-producing *Escherichia coli* according to Evaluation Experiment 1 of the present invention.

DESCRIPTION OF EMBODIMENTS

An isopropyl alcohol-producing *Escherichia coli* of the present invention is an isopropyl alcohol production system *Escherichia coli*, which is equipped with an isopropyl alcohol production system and includes at least one enhanced enzyme activity selected from the group consisting of an enhanced malate dehydrogenase activity, an enhanced NAD(P)$^+$ transhydrogenase (AB-specific) activity, and an enhanced thiolase activity.

The isopropyl alcohol-producing *Escherichia coli* of the present invention has at least one enhanced enzyme activity of the above-mentioned three enzyme activities, and therefore allows rapid and high-yield production of isopropyl alcohol.

Specifically, as the results of various investigations for improving an activity of the isopropyl alcohol production system, the present invention has found that the production rate of isopropyl alcohol as a product obtained by the *Escherichia coli* is increased and the yield of production thereof is improved by enhancing at least any one of an activity of malate dehydrogenase, which is one of the enzymes present in the glucose metabolic pathway, a NAD(P)$^+$ transhydrogenase (AB-specific) activity, which is an enzyme involved in oxidation-reduction of NAD and NADP$^+$, and a thiolase activity, which is one enzyme of the isopropyl alcohol production system.

In the present invention, the expression: "enhancement" of "activity" or "ability" broadly means that the respective enzyme activities in the isopropyl alcohol-producing *Escherichia coli* after enhancement are higher than those before the enhancement.

The method for enhancement is not specifically restricted as long as the activities of the respective enzymes originally present in the isopropyl alcohol-producing *Escherichia coli* are enhanced, and examples of the enhancing method include enhancement by an enzyme gene introduced from outside the bacterial cell, enhancement by enhanced expression of an enzyme gene in the bacterial cell, or a combination thereof.

Specific examples of the enhancement by an enzyme gene introduced from outside the bacterial cell include: introducing a gene encoding a more active enzyme than a host-derived enzyme from outside the bacterial cell of the host bacterium into the bacterial cell so as to add the enzyme activity of the introduced enzyme gene, or so as to replace the enzyme activity of the host-derived enzyme gene with the enzyme activity of the introduced enzyme gene; increasing the number of host-derived enzyme genes or enzyme genes from outside the bacterial cell to two or more; or any combination thereof.

Specific examples of the enhancement by enhanced expression of an enzyme gene in the bacterial cell include introducing a base sequence that enhances the expression of the enzyme gene from outside the bacterial cell of the host bacterium into the bacterial cell; replacing the promoter of the enzyme gene that the host bacterium possesses on its genome with another promoter so as to enhance the expression of the enzyme gene; or any combination thereof.

In the present invention, the term "host" means an *Escherichia coli* that will become the isopropyl alcohol-producing *Escherichia coli* of the present invention as the result of introduction of one or more genes from outside the bacterial cell.

In addition, the scope of the term "process" in the present invention includes an independent process as well as a process that cannot be clearly distinguished from another process but achieves an intended effect of the process.

In the present specification, the range of numerical values described using "to" indicates a range including numerical values described before and after the "to" as a minimum value and a maximum value, respectively.

Hereinafter, the present invention will be described.

The malate dehydrogenase in the present invention is classified under enzyme code number: 1.1.1.40 based on the Report of the Commission on Enzymes, International Union of Biochemistry (I.U.B) and is a generic name of enzymes that catalyze a reaction of producing pyruvic acid and $CO_2$ from L-malic acid.

Examples of the malate dehydrogenase include those derived from a protozoan of the genus *Tritrichomonas* such as *Tritrichomonas vaginalis*, a *Rhizobium* bacterium such as *Rhizobium meliloti*, a *Sulfolobus* bacterium such as *Sulfolobus fataricus*, a bacterium of the genus *Corynebacterium* such as *Corynebacterium glutamicum*, a bacterium of the genus *Escherichia* such as *Escherichia coli*, and a bacterium of the genus *Sinorhizobium* such as *Sinorhizobium meliloti*.

As a gene of the inalate dehydrogenase used in the present invention, a DNA having the base sequence of a gene encoding the malate dehydrogenase of any of the above-mentioned source organisms or a synthetic DNA sequence synthesized based on a known base sequence of the gene can be used. Suitable examples include those derived from prokaryotes such as *Rhizobium* bacteria, *Sulfolobus* bacteria, bacteria of the genus *Corynebacterium*, bacteria of the genus *Escherichia*, and bacteria of the genus *Sinorhizobium*. A DNA having the base sequence of an *Escherichia coli*-derived gene is particularly preferable.

So far, there have been no report that malate dehydrogenase activity and the expression of a gene encoding this enzyme were enhanced with an aim to improve the production of a useful substance. Rather, it is generally thought that, in the production of a substance using a microorganism, improvement of the productivity and yield requires the deletion of the activity of malate dehydrogenase or a gene encoding this enzyme present in the microorganism, as described in WO2009/023493 WO2009/012210, and WO2009/111672. Thus, improvement in the rate and yield of isopropyl alcohol production by enhancing the malate dehydrogenase activity was completely unexpected.

The NAD(P)⁺ transhydrogenase (AB-specific) in the present invention is classified under the enzyme code number: 1.6.1.2 based on the Report of the Commission on Enzymes, International Union of Biochemistry (I.U.B) and is a generic name of enzymes catalyzing a reaction as follows:

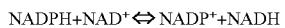

Here, NADP is nicotinamide adenine dinucleotide phosphate, and NADPH represents a reduced form thereof. Further, NAD is nicotinamide adenine dinucleotide, and NADH represents a reduced formed thereof.

Examples of the NAD(P)⁺ transhydrogenase (AB-specific) include those derived from bacteria of the genus *Escherichia* such as *Escherichia coli*, bacteria of the genus *Rhodobacter* such as *Rhodobacter sphaeroides* and *Rhodobacter capsulatus*, and bacteria of the genus *Klebsiella* such as *Klebsiella pneumoniae*.

As a gene of the NAD(P)⁺ transhydrogenase (AB-specific) used in the present invention, a DNA having the base sequence of a gene encoding NAD(P)⁺ transhydrogenase (AB-specific) obtained from any of the above-mentioned source organisms or a synthetic DNA sequence synthesized based on a known base sequence of the gene can be used. Suitable examples thereof include those derived from prokaryotes such as bacteria of the genus *Escherichia*, bacteria of the genus *Rhodobacter*, and bacteria of the genus *Klebsiella*. For example, a DNA having the base sequence of the gene of *Escherichia coli* can be exemplified. A DNA having the base sequence of an *Escherichia coli*-derived gene is particularly preferable.

The thiolase in the present invention is classified under the enzyme code number: 2.3.1.9 based on the Report of the Commission on Enzymes, International Union of Biochemistry (I.U.B) and is a generic name of enzymes that catalyze a reaction of producing acetoacetyl CoA from acetyl CoA.

Examples of such thiolase include those derived from bacteria of the genus *Clostridium* such as *Clostridium acetobutylicum* and *Clostridium beijerinckii*, bacteria of the genus *Escherichia* such as *Escherichia coli*, bacteria of *Halobacterium* species, bacteria of the genus *Zoogloea* such as *Zoogloea ramigera*, *Rhizobium* species, bacteria of the genus *Bradyrhizobium* such as *Bradyrhizobium japonicum*, bacteria of the genus *Candida* such as *Candida tropicalis*, bacteria of the genus *Caulobacter* such as *Caulobacter crescentus*, bacteria of the genus *Streptomyces* such as *Streptomyces collinus*, and bacteria of the genus *Enterococcus* such as *Enterococcus faecalis*.

As a gene of the thiolase used in the present invention, a DNA having the base sequence of a gene encoding thiolase obtained from any of the above-mentioned source organisms or a synthetic DNA sequence synthesized based on a known base sequence of the gene can be used. Suitable examples thereof include DNAs having the base sequences of the genes derived from bacteria of the genus *Clostridium* such as *Clostridium acetobutylicum* and *Clostridium beijerinckii*, bacteria of the genus *Escherichia* such as *Escherichia coli*, bacteria of *Halobacterium* sp., bacteria of the genus *Zoogloea* such as *Zoogloea ramigera*, bacteria of *Rhizobium* sp., bacteria of the genus *Bradyrhizobium* such as *Bradyrhizobium japonicum*, bacteria of the genus *Candida* such as *Candida tropicalis*, bacteria of the genus *Caulobacter* such as *Caulobacter crescentus*, bacteria of the genus *Streptomyces* such as *Streptomyces collinus*, and bacteria of the genus *Enterococcus* such as *Enterococcus faecalis*. More suitable examples include those derived from prokaryotes such as bacteria of the genus *Clostridium* or bacteria of the genus *Escherichia*. A DNA having the base sequence of a gene derived from *Clostridium acetobutylicum* or *Escherichia coli* is particularly preferable.

The isopropyl alcohol-producing *Escherichia coli* of the present invention has at least one enzyme activity from among the enhanced enzyme activities obtained by respectively enhancing the above-described three enzyme activities. Among the three enhanced enzyme activities, the thiolase activity is also one of the enzymes that form the isopropyl alcohol production system, which will be described below. Thus, in a case in which the thiolase activity is included as a target enhanced enzyme activity in the *Escherichia coli*, the thiolase activity needs to be further enhanced. Examples of the enhancement include enhancement of the expression of a gene encoding thiolase in a plasmid or the genome, an increase of the number of copies of thiolase gene, and any combination thereof, as described above.

The isopropyl alcohol-producing *Escherichia coli* in the present invention is an *Escherichia coli* equipped with the isopropyl alcohol production system, and refers to an *Escherichia coli* having an isopropyl alcohol production ability that has been introduced or modified by genetic recombination. Such an isopropyl alcohol production system may be any system that causes *Escherichia coli* of interest to produce isopropyl alcohol.

A preferable example is enhancement of an enzyme activity involved in the production of isopropyl alcohol. In the isopropyl alcohol-producing *Escherichia coli* of the present invention, more preferably, four enzyme activities—an acetoacetic acid decarboxylase activity, an isopropyl alcohol dehydrogenase activity, a CoA transferase activity, and the above-described thiolase activity—are imparted from outside the bacterial cell, or the expression of the four enzyme activities is enhanced in the bacterial cell, or both of these are carried out.

In the present invention, the scope of the expression "by genetic recombination" encompasses all cases in which any change in a base sequence occurs due to the insertion of another DNA into the base sequence of an innate gene, a substitution or deletion of a certain part of the gene, or any of combinations thereof, and encompasses, for example, a change in a base sequence occurring as a result of mutation.

The acetoacetate decarboxylase in the present invention is classified under the enzyme code number: 4.1.1.4 based on the Report of the Commission on Enzymes, International Union of Biochemistry (I.U.B) and is a generic name of enzymes that catalyze a reaction of producing acetone from acetoacetic acid.

Examples of the acetoacetate decarboxylase include those derived from bacteria of the genus *Clostridium* such as *Clostridium acetobutylicum* and *Clostridium beijerinckii*, and bacteria of the genus *Bacillus* such as *Bacillus polymyxa*.

An acetoacetate decarboxylase gene to be introduced into the host bacterium of the present invention may be a DNA having the base sequence of a gene encoding acetoacetate decarboxylase obtained from any of the above-described source organisms or a synthetic DNA sequence synthesized based on a known base sequence of the gene. Suitable examples thereof include those derived from bacteria of the genus *Clostridium* or bacteria of the genus *Bacillus*, and an example is a DNA having the base sequence of a gene derived from *Clostridium acetobutylicum* or *Bacillus polymyxa*. A DNA having the base sequence of a gene derived from *Clostridium acetobutylicum* is particularly preferable.

The isopropyl alcohol dehydrogenase in the present invention is classified under the enzyme code number: 1.1.1.80 based on the Report of the Commission on Enzymes. International Union of Biochemistry (I.U.B) and is a generic name of enzymes that catalyze a reaction of producing isopropyl alcohol from acetone.

Examples of the isopropyl alcohol dehydrogenase include those derived from bacterial of the genus *Clostridium* such as *Clostridium beijerinckii*.

As an isopropyl alcohol dehydrogenase gene to be introduced into the host bacterium of the present invention, a DNA having the base sequence of a gene encoding the isopropyl alcohol dehydrogenase obtained from any of the above-mentioned source organisms or a synthetic DNA sequence synthesized based on a known base sequence of the gene can be used. Suitable examples thereof include those derived from bacteria of the genus *Clostridium*, such as a DNA having the base sequence of a gene derived from *Clostridium beijerinckii*.

The CoA transferase in the present invention is classified under the enzyme code number: 2.8.3.8 based on the Report of the Commission on Enzymes, International Union of Biochemistry (I.U.B) and is a generic name of enzymes that catalyze a reaction of producing acetoacetic acid from acetoacetyl CoA.

Examples of the CoA transferase include those derived from bacteria of the genus *Clostridium* such as *Clostridium acetobutylicum* and *Clostridium beijerinckii*, bacteria of the genus *Roseburia* such as *Roseburia intestinalis*, bacteria of the genus *Faecalibacterium* such as *Faecalibacterium prausnitzii*, bacteria of the genus *Coprococcus*, *Trypanosoma* such as *Trypanosoma brucei*, and bacteria of the genus *Escherichia* such as *Escherichia coli* (the colon *bacillus*).

As a CoA transferase gene used in the present invention, a DNA having the base sequence of a gene encoding the CoA transferase obtained from any of the above-mentioned source organisms or a synthetic DNA sequence synthesized based on a known base sequence of the gene can be used. Suitable examples thereof include DNAs having the base sequences of genes derived from bacteria of the genus *Clostridium* such as *Clostridium acetobutylicum*, bacteria of the genus *Roseburia* such as *Roseburia intestinalis*, bacteria of the genus *Faecalibacterium* such as *Faecalibacterium prausnitzii*, bacteria of the genus *Coprococcus*, *Trypanosoma* such as *Trypanosoma brucei*, and bacteria of the genus *Escherichia* such as *Escherichia coli*. Those derived from bacteria of the genus *Clostridium* or bacteria of the genus *Escherichia* are more preferred. A DNA having the base sequence of a gene derived from *Clostridium acetobutylicum* or *Escherichia coli* is particularly preferable.

As described above, the thiolase used to produce isopropyl alcohol in the present invention is classified under the enzyme code number: 2.3.1.9 based on the Report of the Commission on Enzymes, International Union of Biochemistry (I.U.B) and is the generic name of the enzymes that catalyze the reaction of producing acetoacetyl CoA from acetyl CoA. Regarding details of the thiolase, the above-described details thereof shall apply as they are.

Among the above, it is preferable that each of the four enzymes is derived from at least one selected from the group consisting of a bacterium of the genus *Clostridium*, a bacterium of the genus *Bacillus*, and a bacterium of the genus *Escherichia*, from the viewpoint of enzyme activity. In particular, a case in which acetoacetate decarboxylase and isopropyl alcohol dehydrogenase are derived from a bacterium or bacteria of the genus *Clostridium* and CoA transferase activity and thiolase activity are derived from a bacterium or bacteria of the genus *Escherichia*, and a case in which all of the four enzymes are derived from a bacterium or bacteria of the genus *Clostridium*, are more preferable.

In particular, from the viewpoint of enzyme activity, it is preferable that each of the four enzymes in the present invention is derived from *Clostridium acetobutylicum, Clostridium*

*beijerinckii*, or *Escherichia coli*, it is more preferable that acetoacetate decarboxylase is an enzyme derived from *Clostridium acetobutylicum*, each of CoA transferase and thiolase is an enzyme derived from *Clostridium acetobutylicum* or *Escherichia coli*, and isopropyl alcohol dehydrogenase is an enzyme derived from *Clostridium beijerinckii*. From the viewpoint of enzyme activity, the four enzymes are particularly preferably such that the acetoacetate decarboxylase activity is derived from *Clostridium acetobutylicum*, the isopropyl alcohol dehydrogenase activity is derived from *Clostridium beijerinckii*, and the CoA transferase activity and the thiolase activity are derived from *Escherichia coli*.

In the present invention, as an example of the isopropyl alcohol-producing *Escherichia coli* equipped with the isopropyl alcohol production system including a thiolase activity, a pIPA/B strain or a plaaa/B strain described in WO2009/008377 may be exemplified. In addition, the *Escherichia coli* includes a strain (which may be referred to as pIa/B::atoDAB strain), in which, among the enzymes involving in the production of isopropyl alcohol, the CoA transferase activity and the thiolase activity are enhanced by enhancing the expression of each of these genes in the genome of the *Escherichia coli* and the isopropyl alcohol dehydrogenase activity and the acetoacetic acid decarboxylase activity are enhanced by enhancing the expression of each of these genes by using a plasmid.

In the present invention, it is preferable that an enhanced malate dehydrogenase activity is included as an enhanced enzyme activity from the viewpoint of more effectively improving isopropyl alcohol productivity. It is more preferable that an enhanced malate dehydrogenase activity and an enhanced thiolase activity are included or an enhanced malate dehydrogenase activity and an enhanced NAD(P)$^+$ transhydrogenase (AB-specific) activity are included, and it is most preferable that all of an enhanced malate dehydrogenase activity, an enhanced NAD(P)$^+$ transhydrogenase (AB-specific) activity, and an enhanced thiolase activity are included.

In the present invention, it is most preferable to enhance the expression of respective genes encoding the malate dehydrogenase, the NAD(P)$^+$ transhydrogenase (AB-specific), and the thiolase. This enables drastic increase in the productivity and yield of isopropyl alcohol as compared to a case of enhancing the activity of each enzyme singly.

A preferable embodiment of the isopropyl alcohol-producing *Escherichia coli* in the present invention is a strain obtained by enhancing the malate dehydrogenase activity, or simultaneously enhancing the malate dehydrogenase activity and the activity of the NAD(P)$^+$ transhydrogenase (AB-specific) and/or the thiolase, in the pIPA/B strain, the plaaa/B strain, or the pIa/B::atoDAB strain described above. The thiolase activity in this strain may be an activity achieved by enhancing the expression of a thiolase-encoding gene in the genome as well as enhancing the expression of a thiolase-encoding gene by using a plasmid.

A more preferable embodiment thereof is a strain obtained by enhancing the malate dehydrogenase activity, or simultaneously enhancing the malate dehydrogenase activity and the activity of the NAD(P)$^+$ transhydrogenase (AB-specific) and/or the thiolase, in the pIPA/B strain, the plaaa/B strain, or the pIa/B::atoDAB strain described above. In this strain, the thiolase activity may be an activity achieved by enhancing the expression of a thiolase-encoding gene in the genome as well as enhancing the expression of a thiolase-encoding gene by using a plasmid.

A particularly preferable embodiment thereof is a strain obtained by simultaneously enhancing the malate dehydrogenase activity, the NAD(P)$^+$ transhydrogenase (AB-specific) activity, and the thiolase activity in the pIPA/B strain, the plaaa/B strain, or the pIa/B::atoDAB strain described above. In this strain, the thiolase activity may be an activity achieved by enhancing the expression of a thiolase-encoding gene in the genome as well as enhancing the expression of a thiolase-encoding gene by using a plasmid.

A most preferable embodiment thereof is a strain obtained by simultaneously enhancing the malate dehydrogenase activity, the NAD(P)$^+$ transhydrogenase (AB-specific) activity, and the thiolase activity in the above-described strain or in the pIa/B::atoDAB strain. In this strain, the thiolase activity may be an activity achieved by enhancing the expression of a thiolase-encoding gene in the genome as well as the expression of a thiolase-encoding gene is enhanced by using a plasmid.

The promoter for a gene in the present invention may be any promoter capable of controlling the expression of any of the genes described above. The gene promoter may be a powerful promoter which constitutively functions in a microorganism and of which the expression is hardly suppressed even in the presence of glucose. Specific examples thereof include a promoter of glyceraldehyde-3-phosphate dehydrogenase (which may be hereinafter referred to as GAPDH) and a promoter of serine hydroxymethyltransferase.

The promoter in the present invention refers to a region to which an RNA polymerase having a sigma factor attaches to initiate transcription. For example, a GAPDH promoter derived from *Escherichia coli* is shown in base numbers 397-440 in the base sequence information of GenBank accession number X02662.

CoA transferase genes (atoD and atoA) and a thiolase gene (atoB) derived from *Escherichia coli* form an operon in the order of atoD, atoA, and atoB in the genome of the *Escherichia coli* (*Journal of Baceleriology* Vol. 169 pp 42-52 Lauren Sallus Jenkins et Thus, the expression of the CoA transferase gene and the thiolase gene can be simultaneously controlled by modifying the promoter for atoD.

Accordingly, when the CoA transferase activity and the thiolase activity are those derived from the genomic genes of the host *Escherichia coli*, the expression of both enzyme genes is preferably enhanced by, for example, substitution of another promoter for a promoter responsible for the expression of both enzyme genes, from the viewpoint of acquiring sufficient isopropyl alcohol production ability. Examples of a promoter used to enhance the expression of the CoA transferase activity and the thiolase activity include the above-mentioned *Escherichia coli*-derived GAPDH promoter.

The activities of these enzymes in the present invention may be activities introduced from outside the bacterial cell into the bacterial cell, or activities achieved by enhancing the expression of the enzyme genes by enhancement of the promoter activity for the enzyme genes that the host bacterium possesses in its genome or by substitution of the promoter activity with another promoter.

The introduction of enzyme activity can be performed by, for example, introduction of an enzyme-encoding gene from outside the bacterial cell of the host bacterium into the bacterial cell using a genetic recombination technique. In this case, the enzyme gene to be introduced may be either homologous or heterologous to the host cell. The preparation of a genomic DNA necessary for the introduction of a gene from outside the bacterial cell into the bacterial cell, the cleavage and ligation of DNA, transformation, PCR (polymerase chain reaction), the design and synthesis of oligonucleotides used as primers, etc. can be carried out by methods well known to those skilled in the art. Such methods are described in, for example, Sambrook, J. et al., "Molecular Cloning A Laboratory Manual, Second Edition", Cold Spring Harbor Laboratory Press, (1989).

In the present invention, the *Escherichia coli* having an enhanced enzyme activity refers to an *Escherichia coli* in which the enzyme activity is enhanced by a certain method. Such *Escherichia coli* can be produced by methods such as the introduction of a gene encoding the enzyme and protein from outside the bacterial cell into the bacterial cell using a plasmid according to the same genetic recombination technique as described above, or enhanced expression of an enzyme gene by enhancement of the promoter activity for the enzyme gene in the genome of the host *Escherichia coli* or by substitution of the promoter activity with another promoter.

In the present invention, the term "*Escherichia coli*" means an *Escherichia coli* that can be made to possess the ability to produce isopropyl alcohol from a plant-derived raw material by using a certain means, regardless of whether or not the *E. coli* inherently has the innate ability to produce isopropyl alcohol from a plant-derived raw material.

Herein, the *Escherichia coli* to be subjected to the above-mentioned genetic recombination may be an *Escherichia coli* that does not have the isopropyl alcohol production ability, and may be any *Escherichia coli* capable of introduction and modification of each of the above-described genes.

The *Escherichia coli* may be more preferably an *Escherichia coli* with the isopropyl alcohol production ability that has been imparted in advance, which can achieve more efficient isopropyl alcohol production.

Examples of such an isopropyl alcohol-producing *Escherichia coli* include an isopropyl alcohol-producing *Escherichia coli* to which an acetoacetate decarboxylase activity, an isopropyl alcohol dehydrogenase activity, a CoA transferase activity, and a thiolase activity are imparted, and which can produce isopropyl alcohol to from a plant-derived aw material.

The isopropyl alcohol producing method of the present invention includes producing isopropyl alcohol from a plant-derived raw material using the above-described isopropyl alcohol-producing *Escherichia coli*. Specifically, the isopropyl alcohol producing method of the invention includes a process of contacting the isopropyl alcohol-producing *Escherichia coli* with a plant-derived raw material and culturing the isopropyl alcohol-producing *Escherichia coli*, and a recovery process of recovering isopropyl alcohol obtained by the contact.

The plant-derived raw material used in the isopropyl alcohol producing method is a carbon source obtained from a plant and is not specifically restricted as long as it is a plant-derived raw material. The plant-derived raw material in the present invention refers to an organ such as root, stem, trunk, branch, leaf, flower, or seed, a plant body including them, or a decomposition product of any of the plant organs. In addition, the scope of the plant-derived raw material also encompasses carbon sources that can be utilized as carbon sources by microorganisms during cultivation from among carbon sources obtained from the plant body, the plant organs, or the decomposition products thereof.

General examples of carbon sources that the scope of the plant-derived raw material encompasses include saccharides such as starch, sucrose, glucose, fructose, xylose, and arabinose, wood and herbaceous decomposition products and cellulose hydrolysates containing these ingredients at high proportion, and combinations thereof. In addition, the scope of the carbon source in the present invention also encompasses plant oil-derived glycerin or fatty acid.

Preferable examples of the plant-derived raw material in the present invention include agricultural products such as crops, corn, rice, wheat, soybean, sugarcane, beet, cotton, and combinations thereof. The usage form as a raw material is not particularly limited, and may be an unprocessed product, juice, a crushed product, or the like. It is also possible to use only the above-described carbon source as the raw material.

At the culturing process, the isopropyl alcohol-producing *Escherichia coli* and the plant-derived raw material are contacted with each other generally by culturing the isopropyl alcohol-producing *Escherichia coli* in a culture medium including the plant-derived raw material.

The density of contact between the plant-derived raw material and the isopropyl alcohol-producing *Escherichia coli* varies depending on the activity of the isopropyl alcohol-producing *Escherichia coli*. In general, the concentration of the plant-derived raw material in the culture medium may be set such that the initial sugar concentration in terms of glucose may be set to 20% by mass or less with respect to the total mass of the mixture, and, from the viewpoint of the sugar resistance of the *Escherichia coli*, the initial sugar concentration is preferably set to 15% by mass or less. Other components may be added in amounts usually added to culture media of microorganism, without particular restriction.

The content of the isopropyl alcohol-producing *Escherichia coli* in the culture medium varies depending on the kind and activity of the *Escherichia coli*. In general, the initial bacterial concentration may be set to be from 0.1 to 30% by mass with respect to the culture medium, and, from the viewpoint of controlling culture conditions, the initial bacterial concentration is preferably set to be from 1 to 10% by mass with respect to the culture medium.

The culture medium to be used for cultivation of the isopropyl alcohol-producing *Escherichia coli* may be any commonly used culture medium that includes a carbon source, a nitrogen source, and an inorganic ion, as well as organic minor elements, nucleic acid, vitamins etc. required by the microorganism for the production of lactic acid, without particular restriction.

The culture conditions for the culturing in the invention are not specifically restricted, and cultivation may be carried out, for example, under aerobic conditions with appropriate pH and temperature control within a range of pH 4 to 9, preferably pH 6 to 8, and a temperature of 20 to 50° C., preferably 25 to 42° C.

The aeration amount of gas into the mixture is not particularly restricted. In a case in which only air is used as the gas, the aeration amount is generally from 0.02 to 2.0 vvm (vvm; aeration volume [mL]/liquid volume [mL]/time [min]), and preferably from 0.1 to 2.0 vvm from the viewpoint of suppressing physical damage to the *Escherichia coli*.

The culturing process may be continued from the start of the cultivation until the plant-derived raw material in the mixture is depleted or until the activity of the isopropyl alcohol-producing *Escherichia coli* disappears. The duration of the culturing process varies depending on the number and activity of the isopropyl alcohol-producing *Escherichia coli* and the amount of the plant-derived raw material, but the duration may generally be 1 hour or more, and preferably 4 hours or more. Although the culturing period can be unlimitedly continued by additional feeding of the plant-derived raw material or the isopropyl alcohol-producing *Escherichia coli*, the culturing period may generally be set to 5 days or less, and preferably 72 hours or less, from the viewpoint of processing efficiency. Regarding other conditions, conditions used for usual cultivation may directly be applied.

The method for recovering isopropyl alcohol accumulated in the culture medium is not particularly restricted. For example, a method may be employed in which the bacterial cells are removed from the culture medium by, for example, centrifugation, and then isopropyl alcohol is separated by a usual separation technique such as evaporation or film separation.

The isopropyl alcohol producing method of the present invention may include, before the culturing process for isopropyl alcohol production, a preculturing process of obtaining an appropriate number or appropriate active state of isopropyl alcohol-producing *Escherichia coli* cells for use. The preculturing process may be any cultivation under usually-employed culture conditions suitable for the kind of isopropyl alcohol-producing bacterium.

The isopropyl alcohol producing method of the present invention preferably includes a culturing process of culturing the isopropyl alcohol-producing *Escherichia coli* while supplying a gas into a mixture containing the isopropyl alcohol-producing bacterium and a plant-derived raw material, and a recovery process of separating and recovering isopropyl alcohol produced by the culturing from the mixture.

According to this method, the *Escherichia coli* for production is cultured while supplying a gas into the mixture (aeration culturing). By the aeration culturing, the isopropyl alcohol produced is released into the mixture and evaporates from the mixture, as a result of which the isopropyl alcohol produced can be easily separated from the mixture. Further, since the isopropyl alcohol produced is continuously separated from the mixture, increase in the concentration of isopropyl alcohol in the mixture can be suppressed. Thus, there is no particular need to consider the resistance of the isopropyl alcohol-producing *Escherichia coli* against isopropyl alcohol.

The mixture in the present method may contain a basic culture medium generally used for culturing *Escherichia coli* as the major component. Regarding culture conditions, the details thereof described above shall directly apply.

At the recovery process, the isopropyl alcohol produced in the culturing process and separated from the mixture is recovered. The recovery method may be any method that can collect isopropyl alcohol in the gaseous or droplet form that has been evaporated from the mixture by usual cultivation. Examples of such a method include recovering isopropyl alcohol in a collection member such as a commonly used airtight container. In particular, the recovery method is preferably includes bringing a capture liquid for capturing isopropyl alcohol into contact with isopropyl alcohol separated from the mixture, from the viewpoint of allowing high-purity recovery of only isopropyl alcohol.

In this method, isopropyl alcohol can be recovered in the state of being dissolved in the capture liquid or the mixture. Examples of such a recovery method include a method described in the pamphlet of WO 2009/008377. The recovered isopropyl alcohol can be identified using a usual detection means such as HPLC. The recovered isopropyl alcohol may further be purified, as necessary. The purification method may be, for example, distillation or the like.

When the recovered isopropyl alcohol is in the state of aqueous solution, the isopropyl alcohol producing method may further include a dehydration process in addition to the recovery process. The dehydration of isopropyl alcohol may be performed by a usual method.

An example of an apparatus applicable to the method for producing isopropyl alcohol that can be recovered in the form of being dissolved in the capture liquid or the mixture is a production apparatus shown in FIG. 1 of the pamphlet of WO2009/008377.

In the production apparatus, an injection tube for injecting a gas from outside the apparatus is connected to a culture tank that houses a culture medium including an isopropyl alcohol-producing bacterium and a plant-derived raw material, thereby allowing aeration into the culture medium.

In addition, the culture tank is connected to, via a connection tube, a trap tank that houses a trap liquid as a capture liquid. In this case, a gas or a liquid that has moved to the trap tank contacts with the trap liquid to cause bubbling.

As a result of this, isopropyl alcohol produced in the culture tank by aeration culture is evaporated by the aeration and easily separated from the culture medium, and is captured by the trap liquid in the trap tank. As a result, isopropyl alcohol can be produced continuously and easily in a more purified form.

According to the isopropyl alcohol producing method of the present invention, isopropyl alcohol can be rapidly produced, and the production rate usually obtained by the same method is higher than in a case in which the present invention is not applied. The production rate varies depending on the conditions for the production method and the state of the isopropyl alcohol-producing *Escherichia coli* to be used, but a production rate of from 0.7 to 2.0 g/L/hr, preferably 0.9 to 1.9 g/L/hr, can be obtained. Further, according to the isopropyl alcohol producing method of the present invention, isopropyl alcohol can be effectively produced from glucose, and the yield usually obtained by the same method is higher than in a case in which the present invention is not applied. The yield varies depending on the conditions for the production method and the state of the isopropyl alcohol-producing *Escherichia coli* to be used, and a yield of from 51 to 80%, preferably from 51 to 66%, can be obtained at the termination of the culturing process.

In the present invention, the term "yield" represents a conversion rate based on a stoichiometric equation for the conversion of glucose as a substrate to isopropyl alcohol as a metabolite. In the isopropyl alcohol-producing *Escherichia coli*, 1 mol of isopropyl alcohol is produced from 1 mol of glucose. Accordingly, considering the molecular weights of glucose and isopropyl alcohol (glucose=180; isopropyl alcohol=60), even if 180 g of glucose is all converted to isopropyl alcohol, the amount of isopropyl alcohol produced will be only 60 g, and can never be more than that. This theoretically maximum conversion rate is defined as yield 100% in the present invention.

As described above, the isopropyl alcohol-producing *Escherichia coli* of the present invention can produce isopropyl alcohol rapidly with high yield. Therefore, for example, when producing isopropyl alcohol using the *Escherichia coli* of the present invention as a catalyst, 97 g/L or more of isopropyl alcohol can be accumulated in 72 hours of culture, so that a remarkably higher productivity than in the conventional catalysts can be achieved.

EXAMPLES

Hereinafter, examples of the present invention will be described, but the invention is not restricted thereto. In the description, "%" is based on mass unless otherwise specified.

Example 1

[B::pntA]: Production of *Escherichia Coli* B pnt Genome-Enhanced Strain

A pntA gene promoter in the genome of an *Escherichia coli* B strain was substituted with a GAPDH promoter to enhance the expression of pntA gene.

The entire base sequence of the genomic DNA of an *Escherichia coli* MG1655 strain is known (GenBank accession number U00096), and the base sequence of a gene encoding an NAD(P)$^+$ transhydrogenase (AB-specific) α subunit of *Escherichia coli* (which may be hereinafter abbreviated to pntA) has also been reported (GenBank accession number X04195). In addition, it is known that pntA and a membrane transhydrogenase β subunit (pntB) form an operon in the genomic DNA of *Escherichia coli* MG1655 strain.

As a base sequence of a promoter necessary to allow the expression of the gene, a promoter sequence of glyceraldehyde 3-phosphate dehydrogenase (which may be hereinafter referred to as GAPDH) derived from *Escherichia coli* described in 397 to 440 in the base sequence information of GenBank accession number X02662 can be used. To obtain the GAPDH promoter, amplification by PCR method was carried out using the genomic DNA of *Escherichia coli* MG1655 strain as a template, and using cgctcaattgcaatgattgacacgattccg (SEQ ID NO: 1) and acagaattcgctatttgttagtgaataaaagg (SEQ ID NO: 2). The DNA fragment obtained was digested with restriction enzymes MfeI and EcoRI to obtain a DNA fragment with a size of approximately 100 bp encoding the GAPDH promoter. The obtained DNA fragment and a fragment obtained by digesting plasmid pUC19 (GenBank accession number X02514) with restriction enzyme EcoRI and further processing with alkaline phosphatase were mixed together, and are ligated using a ligase. *Escherichia coli* DH5α competent cells (DNA-903 manufactured by Toyobo Co., Ltd.) were transformed with the resultant ligation product, as a result of which a transformant growing on an LB agar plate containing 50 μg/mL of ampicillin was obtained. Ten of the obtained colonies were each cultured overnight at 37° C. in an LB liquid medium containing 50 μg/mL of ampicillin, and plasmids were recovered. A plasmid from which the GAPDH promoter was not cut out when digested with the restriction enzymes EcoRI and KpnI was selected, and the DNA sequence thereof was confirmed. The plasmid in which the GAPDH promoter was appropriately inserted was named pUCgapP. The pUCgapP obtained was digested with restriction enzymes EcoRI and HindIII.

Furthermore, in order to obtain a pntA, amplification by PCR was carried out using the genomic DNA of *Escherichia coli* MG1655 strain as a template, and using gcagcaattgctggtggaacatatgcgaattggcataccaag (SEQ ID NO: 3) and ggacaagcttaatttttgcggaacattttcagc (SEQ ID NO: 4). The DNA fragment obtained was digested with restriction enzymes MfeI and HindIII to obtain a pntA fragment with a size of approximately 1.6 kbp. This DNA fragment was mixed with the pUCgapP that had been previously digested with restriction enzymes EcoRI and HindIII, and ligated using a ligase. *Escherichia coli* DH5α competent cells (DNA-903 manufactured by Toyobo Co., Ltd.) were transformed with the ligation product, as a result of which a transformant growing on an LB agar plate containing 50 μg/mL of ampicillin was obtained. A plasmid was recovered from the bacterial cells obtained, and the correct insertion of pntA was confirmed. This plasmid was named pGAPpntA.

Here, *Escherichia coli* MG1655 strain is available from the American Type Culture Collection.

As mentioned above, the genomic DNA of the *Escherichia coli* MG1655 strain has been clarified, and the base sequence near pntA has also been reported. Using atggtacegcagtaatacgctggttgc (SEQ ID NO: 5) and cctctagacttccatcggttttattgatgatgg (SEQ ID NO: 6) prepared based on the gene information of the near 5' region of pntA of the *Escherichia coli* MGI 655 strain, PCR was carried out with the genomic DNA template of the *Escherichia coli* MG1655 strain to amplify a DNA fragment with a size of approximately 1.0 kbp. This DNA fragment was treated with restriction enzymes KpnI and XbaI.

In addition, using a primer of ggtctagagcaatgattgacacgattccg (SEQ ID NO: 7) prepared based on the sequence information of the GAPDH promoter of the *Escherichia coli* MG1655 strain and the primer of SEQ ID NO: 4 prepared based on the sequence information of pntA of the *Escherichia coli* MG1655 strain, PCR was carried out using, as a template, the previously prepared expression vector pGAPpntA, as a result of which a DNA fragment with a size of approximately 1.7 kbp including the GAPDH promoter and pntA was obtained. The DNA fragment was treated with restriction enzymes XbaI and HindIII.

The DNA fragment of the near 5' region of pntA and the DNA fragment including the GAPDH promoter and pntA thus obtained were mixed with a DNA fragment obtained by digesting a temperature-sensitive plasmid pTH18cs1 (GenBank accession number AB019610) [Hashimoto-Gotoh, T., Gene, 241, 185-191 (2000)] with KpnI and HindIII, and then ligated using a ligase. DH5α strain was transformed with the ligation product, as a result of which a transformant growing at 30° C. on an LB agar plate containing 10 μg/ml of chloramphenicol was obtained. The colonies obtained were cultured overnight at 30° C. in an LB liquid medium containing 10 μg/ml of chloramphenicol. Then, a plasmid was recovered from the bacterial cells obtained, and the proper insertion of the near 5' region of pntA, the GAPDH promoter and pntA was confirmed. *Escherichia coli* B strain (ATCC11303) was transformed with this plasmid, and cultured overnight at 30° C. on an LB agar plate containing 10 μg/ml of chloramphenicol to obtain a transformant. The transformant obtained was inoculated in an LB liquid medium containing 10 μg/ml of chloramphenicol, and cultured overnight at 30° C. The cultured bacterial cells obtained were applied onto an LB agar plate containing 10 μg/ml of chloramphenicol, and cultured at 42° C. to obtain colonies. The colonies obtained were cultured in an LB liquid medium containing no antibiotic at 30° C. for 4 hours, and applied onto an LB agar plate containing no antibiotic, as a result of which colonies capable of growing at 42° C. were obtained.

From the colonies that appeared, 100 colonies were randomly picked up. Each of them was allowed to grow on an LB agar plate containing no antibiotic and on an LB agar plate containing 10 μg/ml of chloramphenicol, and chloramphenicol-sensitive clones were selected. Further, from the genomic DNA of these clones, a fragment with a size of approximately 1.7 kbp including the GAPDH promoter and pntA was amplified by PCR, and then a strain in which the pntA promoter region was substituted with the GAPDH promoter was selected. A clone satisfying all the above was named *Escherichia coli* B pntA-deleted GAPppntA genome-inserted strain (which may be hereinafter abbreviated to B::pnt strain).

Here, *Escherichia coli* B strain (ATCC11303) is available from the American Type Culture Collection, which is a bank of cells, microorganisms, and genes.

Example 2

[pGAP-Iaaa/B::pnt]: Preparation of *Escherichia Coli* B pnt Genome-Enhanced Strain to which Expression Vector for *Escherichia coli*-Derived Thiolase Gene, *Escherichia coli*-Derived CoA Transferase Gene, Acetoacetate Decarboxylase Gene Derived from Bacterium of the Genus *Clostridium*, and Isopropyl Alcohol Dehydrogenase Gene Derived from Bacterium of the Genus *Clostridium* was Introduced An isopropyl alcohol-producing *Escherichia coli* having enhanced expression of NAD(P)$^+$ transhydrogenase (AB-specific) gene (pnt) was prepared as follows.

The B::pnt strain produced in Example 1 was transformed with pGAP-Iaaa described in Example 4 of WO2009/008377, to obtain a pGAP-Iaaa/B::pnt strain. The pGAP-Iaaa is an expression vector plasmid capable of enhancing the expression of an *Escherichia coli*-derived thiolase gene, an *Escherichia coli*-derived CoA transferase gene, a *Clostridium acetobutylicum*-derived acetoacetate decarboxylase gene, and a *Clostridium beijerinckii*-derived isopropyl alcohol dehydrogenase gene using the promoter of *Escherichia coli*-derived glyceraldehyde-3-phosphate dehydrogenase (GAPDH). The method for preparing pGAP-Iaaa is described in Example 4 of WO2009/008377.

Example 3

[B::atoDAB]: Preparation of *Escherichia coli* B atoDAB Genome-Enhanced Strain

The CoA transferase genes (atoD and atoA) and the thiolase gene (atoB) derived from *Escherichia coli* form an operon in the genome of the *Escherichia coli* in the order of atoD, atoA, and atoB (*Journal of Baceteriology* Vol. 169 pp 42-52 Lauren Sallus Jenkins et al). Accordingly, by modifying the promoter of atoD, the expression of the CoA transferase gene and the thiolase gene can be simultaneously controlled. Thus, the promoter of atoD gene in the genome of the host *Escherichia coli* was substituted with the GAPDH promoter to prepare an *Escherichia coli* having enhanced expression of atoD gene, atoA gene, and atoB gene.

The entire base sequence of the genomic DNA of the *Escherichia coli* MG1655 strain is known (GenBank accession number U00096), and the base sequence of a gene (which may be hereinafter abbreviated to atoD) encoding a CoA transferase α subunit of the *Escherichia coli* MG1655 strain has also been reported. Specifically, atoD is described in 2321469 to 2322131 of the genome sequence of the *Escherichia coli* MG1655 strain shown at GenBank accession number U00096.

As a base sequence of a promoter necessary to allow the expression of the above gene, a promoter sequence of glyceraldehyde 3-phosphate dehydrogenase (GAPDH) derived from *Escherichia coli* described in 397 to 440 in the base sequence information of GenBank accession number X02662 can be used. In order to obtain the GAPDH promoter, amplification by PCR was carried out using the genomic DNA of *Escherichia coli* MG1655 strain as a template and using cgctcaattgcaatgattgacacgattccg (SEQ ID NO: 1) and acagaattcgctatttgttagtgaataaaagg (SEQ ID NO: 2). The DNA fragment obtained was digested with restriction enzymes MfeI and EcoRI to obtain a DNA fragment with the size of approximately 100 bp encoding the GAPDH promoter. The DNA fragment obtained was digested with restriction enzymes MfeI and EcoRI to obtain a DNA fragment with a size of approximately 100 bp encoding the GAPDH promoter. The DNA fragment obtained and a fragment obtained by digesting plasmid pUC19 (GenBank accession number X02514) with restriction enzyme EcoRI and further treating with alkaline phosphatase were mixed together, and ligated using a ligase. *Escherichia coli* DH5α competent cells (DNA-903 manufactured by Toyobo Co., Ltd.) were transformed with the ligation product, as a result of which a transformant growing on an LB agar plate containing 50 µg/mL of ampicillin was obtained. Ten of the obtained colonies were each cultured overnight at 37° C. in an LB liquid medium containing 50 µg/mL of ampicillin, and plasmids were recovered. A plasmid from which the GAPDH promoter was not cut out when digested with restriction enzymes EcoRI and KpnI was selected. The DNA sequence thereof was confirmed, and a plasmid in which the GAPDH promoter was properly inserted was named pUCgapP. The pUCgapP obtained was digested with restriction enzymes EcoRI and KpnI.

Furthermore, to obtain atoD, using the genomic DNA of *Escherichia coli* MG1655 strain as a template, amplification was performed by PCR with cgaattcgctggtggaacatatgaaaacaaaattgatgacattacaagac (SEQ ID NO: 8) and gcggtacct-tatttgctctcctgtgaaacg (SEQ ID NO:9). The obtained DNA fragment was digested with the restriction enzymes EcoRI and KpnI to obtain an atoD fragment with a size of approximately 690 bp. The DNA fragment was mixed with the pUCgapP that had been previously digested with the restriction enzymes EcoRI and KpnI to be ligated using a ligase, and transformed *Escherichia coli* DH5α competent cells (DNA-903 manufactured by Toyobo Co., Ltd.) to obtain a transformant growing on an LB agar plate containing 50 µg/mL of ampicillin. A plasmid was recovered from the obtained bacterial cells and confirmation was made as to whether atoD was appropriately inserted. The plasmid was named pGAPatoD.

Here, *Escherichia coli* MG1655 strain is available from the American Type Culture Collection.

As mentioned above, the base sequence of atoD in the genomic DNA of the *Escherichia coli* MG1655 strain has also been reported. Using gctctagatgctgaaatccactagtcttgtc (SEQ ID NO: 10) and tactgcagcgttccagcaccttatcaacc (SEQ ID NO: 11) prepared based on the gene information of the near 5' region of atoD in the *Escherichia coli* MG1655 strain, PCR was carried out with the genomic DNA template of the *Escherichia coli* MG1655 strain to amplify a DNA fragment with a size of approximately 1.1 kbp.

In addition, using a primer of ggtctagagcaatgattgacacgattccg (SEQ ID NO: 12) prepared based on the sequence information of the GAPDH promoter of the *Escherichia coli* MG1655 strain and the primer of SEQ ID NO: 9 prepared based on the sequence information of atoD of the *Escherichia coli* MG1655 strain, PCR was carried out using, as a template, the previously prepared expression vector pGAPatoD, to obtain a DNA fragment with a size of approximately 790 bp including the GAPDH promoter and atoD.

The fragments thus obtained were digested with restriction enzymes PstI and XbaI, and with restriction enzymes XbaI and KpnI, respectively, and mixed with a fragment obtained by digesting the temperature-sensitive plasmid pTH18cs1 (GenBank accession number AB019610) [Hashimoto-Gotoh, T., Gene, 241, 185-191 (2000)] with PstI and KpnI, and ligated using a ligase, DH5α strain was transformed with the ligation product, as a result of which a transformant growing at 30° C. on an LB agar plate containing 10 µg/ml of chloramphenicol was obtained. The colonies obtained were cultured overnight at 30° C. in an LB liquid medium containing 10 µg/ml of chloramphenicol, and then, a plasmid was recovered from the bacterial cells obtained. *Escherichia coli* B strain (ATCC11303) was transformed with this plasmid, and cultured overnight at 30° C. on an LB agar plate containing 10 μg/ml of chloramphenicol to obtain a transformant. The obtained transformant was inoculated in an LB liquid medium containing 10 μg/ml of chloramphenicol, and cultured overnight at 30° C. The cultured bacterial cells obtained were applied onto an LB agar plate containing 10 μg/ml of chloramphenicol, and cultured at 42° C. to obtain colonies. The obtained colonies were cultured in an LB liquid medium containing no antibiotic at 30° C. for 2 hours and applied onto an LB agar plate containing no antibiotic, as a result of which colonies capable of growing at 42° C. were obtained.

From the colonies that appeared, 100 colonies were randomly picked up. Each of them was allowed to grow on an LB agar plate containing no antibiotic and on an LB agar plate containing 10 μg/ml of chloramphenicol, and then chloramphenicol-sensitive clones were selected. Further, from the chromosome DNA of these clones, a fragment with a size of approximately 790 bp including the GAPDH promoter and atoD was amplified by PCR, and a strain in which the atoD promoter region was substituted with the GAPDH promoter was selected. A clone satisfying all the above was named *Escherichia coli* B atoD-deleted GAPpatoD genome-inserted strain (which may be hereinafter abbreviated to B::atoDAB strain).

Example 4

Construction of Expression Vector for Acetoacetate Decarboxylase Gene Derived from Bacterium of the Genus *Clostridium* and Isopropyl Alcohol Dehydrogenase Gene Derived from Bacterium of the Genus *Clostridium*

In order to obtain an isopropyl alcohol dehydrogenase gene (IPAdh), amplification by PCR was carried out using the genomic DNA of *Clostridium beijerinckii* NRRL B-593 as a template and using aatatgcatgctggtggaacatat-gaaaggattgcaatgctagg (SEQ ID NO: 13) and gcggatcccte-gagttataatataactactgctttaattaagtc (SEQ ID NO: 14). The DNA fragment obtained was digested with restriction enzymes SphI and BamHI to obtain an isopropyl alcohol dehydrogenase fragment with a size of approximately 1.1 kbp. The DNA fragment obtained was mixed with a fragment obtained by digesting pBRgapP (described in Example 4 of WO2009/008377) with restriction enzymes SphI and BamHI. The mixture was ligated using a ligase, and *Escherichia coli* DH5α competent cells (DNA-903 manufactured by Toyobo Co., Ltd.) were transformed with the ligation product, as a result of which a transformant growing on an LB agar plate containing 50 μg/mL of ampicillin was obtained. The obtained colonies were cultured overnight at 37° C. in an LB liquid medium containing 50 μg/ml, of ampicillin. A plasmid was recovered from the obtained bacterial cells, and proper insertion of IPAdh was confirmed. This plasmid was named pGAP-IPAdh.

In order to obtain an acetoacetate decarboxylase gene (adc), amplification by PCR was carried out using the genomic DNA of *Clostridium acetobutylicum* ATCC824 as a template. The DNA fragment obtained was digested with restriction enzymes to obtain an acetoacetate decarboxylase fragment with a size of approximately 700 bp. The obtained DNA fragment was mixed with a fragment obtained by digesting the previously prepared plasmid pGAP-IPAdh with restriction enzymes. The mixture was ligated using a ligase, and *Escherichia coli* DH5α competent cells (DNA-903 manufactured by Toyobo Co., Ltd.) were transformed with the ligation product, as a result of which a transformant growing on an LB agar plate containing 50 μg/mL of ampicillin was obtained. The obtained colonies were cultured overnight at 37° C. in an LB liquid medium containing 50 μg/mL of ampicillin. A plasmid was recovered from the bacterial cells obtained, and proper insertion of adc was confirmed. This plasmid was named pGAP-Ia.

Here, *Clostridium beijerinckii* NRRL B-593 is available from the VTT Culture Collection, which is a bank of cells and microorganisms.

Example 5

[pGAP-Ia-gapP-atoB]: Construction of Expression Vector for Acetoacetate Decarboxylase Gene Derived from Bacterium of the Genus *Clostridium*, Isopropyl Alcohol Dehydrogenase Gene Derived from Bacterium of the Genus *Clostridium*, and *Escherichia coli*-Derived Thiolase Gene The entire base sequence of the genomic DNA of the *Escherichia coli* B strain is known (GenBank accession number CP000819), and the base sequence of a gene encoding thiolase (acetyl-CoA C-acetyltransferase) of *Escherichia coli* (atoB) has also been reported (GenBank accession number U08465). In order to perform cloning of atoB (1,185 bp), two oligonucleotide primers were synthesized.

The genomic DNA of *Escherichia coil* B strain (ATCC11303) was prepared using a DNeasy Tissue kit manufactured by QIAGEN Co. Ltd. Using the obtained genomic DNA as a template, a DNA fragment with a size of approximately 1.2 kb (which may be hereinafter referred to as atoB fragment) was amplified by PCR. The atoB fragment was separated and recovered by agarose gel electrophoresis, and digested with restriction enzymes. The digestion fragment was mixed with an restriction enzymes digested product of pBRgapP, and the mixture was reacted with T4DNA ligase. *Escherichia coli* DH5α competent cells (manufactured by Toyobo Co., Ltd.) was transformed with the ligation product, as a result of which a transformant growing at 37° C. on an LB agar plate containing 50 μg/ml of ampicillin was obtained. The colonies obtained were cultured overnight at 37° C. in an LB liquid medium containing 50 μg/mL of ampicillin. A plasmid was recovered from the bacterial cells obtained, and proper insertion of atoB was confirmed. This plasmid was named pGAP-atoB. The plasmid pGAP-atoB obtained was digested with restriction enzymes BglII and BamHI, and a fragment including the GAPDH promoter and atoB was separated and recovered by agarose gel electrophoresis. This fragment was named gapP-atoB. The fragment gapP-atoB was mixed with a fragment obtained by digesting the plasmid pGAP-Ia prepared in Example 4 with a restriction enzyme. The mixture was ligated using a ligase, and *Escherichia coli* DH5α competent cells (DNA-903 manufactured by Toyobo Co., Ltd.) was transformed with the ligation product, as a result of which a transfonnant growing on an LB agar plate containing 50 μg/mL of ampicillin was obtained. The colonies obtained were cultured overnight at 37° C. in an LB liquid medium containing 50 μg/mL of ampicillin. A plasmid was recovered from the bacterial cells obtained, and proper insertion of gapP-atoB was confirmed. This plasmid was named pGAP-Ia-gapP-atoB.

Example 6

[pGAP-Ia-gapP-atoB/B::atoDAB Strain]: Preparation of *Escherichia coli* B atoDAB Genome-Enhanced Strain by Introduction of pGAP-Ia-gapP-atoB The B::atoDAB strain prepared in Example 3 was transformed with the pGAP-Ia-gapP-atoB described in Example 5 above, to obtain an isopropyl alcohol-producing *Escherichia coli* pGAP-Ia-gapP-atoB/B::atoDAB strain in which the expression of the thiolase gene (atoB) is enhanced in the genome as well as enhanced by using the plasmid.

Example 7

[pGAP-Ia-maeB]: Construction of Expression Vector for Acetoacetate Decarboxylase Gene Derived from Bacterium of the Genus *Clostridium*, Isopropyl Alcohol Dehydrogenase Gene Derived from Bacterium of the Genus *Clostridium*, and *Escherichia Coli*-Derived Malate Dehydrogenase Gene In order to obtain a malate dehydrogenase gene, amplification by PCR was carried out using the genome DNA of the *Escherichia coil* B strain (ATCC11303) as a template. The DNA fragment obtained was digested with restriction enzymes to obtain a malate dehydrogenase fragment with a size of approximately 2300 bp. The obtained DNA fragment was mixed with a fragment obtained by digesting the plasmid pGAP-Ia prepared in Example 4 with restriction enzymes, and the mixture was ligated using a ligase. *Escherichia coli* DH5α competent cells (DNA-903 manufactured by Toyobo Co., Ltd.) were transformed with the ligation product, as a result of which a transformant growing on an LB agar plate containing 50 μg/mL of ampicillin was obtained. The colonies obtained were cultured overnight at 37° C. in an LB liquid medium containing 50 μg/mL of ampicillin. A plasmid was recovered from the bacterial cells obtained, and proper insertion of the malate dehydrogenase gene was confirmed. This plasmid was named pGAP-Ia-maeB.

Example 8

[pGAP-Ia-maeB/B::atoDAB Strain]: Preparation of *Escherichia coli* B atoDAB Genome-Enhanced Strain by Introduction of pGAP-Ia-maeB The B::atoDAB strain prepared in Example 3 was transformed with the pGAP-Ia-maeB described in Example 7 above, to obtain an isopropyl alcohol-producing *Escherichia coli* pGAP-Ia-maeB/B::atoDAB strain having enhanced expression of the malate dehydrogenase gene (maeB).

Example 9

Construction of Expression Vector for Acetoacetate Decarboxylase Gene Derived from Bacterium of the Genus *Clostridium*, Isopropyl Alcohol Dehydrogenase Gene Derived from Bacterium of the Genus *Clostridium, Escherichia coli*-Derived Malate Dehydrogenase Gene, and *Escherichia Coli*-Derived Thiolase Gene A fragment obtained by digesting the plasmid pGAP-Ia-maeB produced in Example 7 above with a restriction enzyme and the DNA fragment gapP-atoB obtained in the same manner as in Example 5 were mixed together, and ligated using a ligase. Then, *Escherichia coli* DH5α competent cells (DNA-903 manufactured by Toyobo Co., Ltd.) was transformed with the ligation product, as a result of which a transformant growing on an LB agar plate containing 50 μg/mL of ampicillin was obtained. The colonies obtained were cultured overnight at 37° C. in an LB liquid medium containing 50 μg/mL of ampicillin. A plasmid was recovered from the bacterial cells obtained, and proper insertion of gapP-atoB was confirmed. This plasmid was named pGAP-Ia-maeB-gapP-atoB.

Example 10

[pGAP-Ia-maeB-gapP-atoB/B::atoDAB Strain]: Preparation of *Escherichia coli* B atoDAB Genome-Enhanced Strain by Introduction of pGAP-Ia-maeB-gapP-atoB The B::atoDAB strain prepared in Example 3 was transformed with the pGAP-Ia-maeB-gapP-atoB described in Example 9 above, to obtain an isopropyl alcohol-producing *Escherichia coli* pGAP-Ia-maeB-atoB/B::atoDAB strain having enhanced expression of both the malate dehydrogenase gene (maeB) and the thiolase gene (atoB).

Example 11

[B::atoDAB::pnt] Preparation of *Escherichia coli* B atoDAB and pnt-Genome Enhanced Strain The B::atoDAB strain prepared in Example 3 was transformed with a plasmid obtained by introducing the DNA fragment of the pntA near-5' region and the DNA fragment including the GAPDH promoter and pntA into the temperature-sensitive plasmid pTH18cs1 in the same manner as in Example 1, and was cultured overnight at 30° C. on an LB agar plate containing 10 μg/ml of chloramphenicol, to obtain a transformant. The obtained transformant was inoculated in an LB liquid medium containing 10 μg/ml of chloramphenicol, and cultured overnight at 30° C. The cultured bacterial cells obtained were applied onto an LB agar plate containing 10 μg/ml of chloramphenicol, and cultured at 42° C. to obtain colonies. The obtained colonies were cultured in an LB liquid medium containing no antibiotic at 30° C. for 2 hours, and applied onto an LB agar plate containing no antibiotic, as a result of which colonies capable of growing at 42° C. were obtained.

From the colonies that appeared, 100 colonies were randomly picked up. Each of them was allowed to grow on an LB agar plate containing no antibiotic and on an LB agar plate containing 10 μg/ml of chloramphenicol, and chloramphenicol-sensitive clones were selected. Further, from the chromosome DNA of those clones, a fragment with a size of approximately 1.7 kbp including the GAPDH promoter and pntA was amplified by PCR, and a strain in which the pntA promoter region was substituted with the GAPDH promoter was selected. A clone satisfying all the above was named *Escherichia coli* B atoD-deleted GAPpatoDGAPppntA genome-inserted strain (which may be hereinafter abbreviated to B::atoDAB::pnt strain).

Example 12

[pGAP-Ia-maeB/B::atoDAB::pnt]: Preparation of *Escherichia Coli* B atoDAB and pnt Enhanced Strain by Introduction of pGAP-Ia-maeB The B::atoDAB::pnt strain prepared in Example 11 was transformed with the pGAP-Ia-maeB described in Example 7, to obtain an isopropyl alcohol-producing *Escherichia coli* pGAP-Ia-maeB/B::atoDAB::pnt strain having enhanced expression of both the malate dehydrogenase gene (maeB) and the NAD(P)$^+$ transhydrogenase (AB-specific) gene (pnt).

Example 13

[pGAP-Ia-gapP-atoB/B::atoDAB::pnt]: Preparation of *Escherichia Coli* B atoDAB and pnt Enhanced Strain by Introduction of pGAP-la-gapP-atoB The B::atoDAB::pnt strain prepared in Example 11 was transformed with the pGAP-Ia-gapP-atoB described in Example 5, to obtain an isopropyl alcohol-producing *Escherichia coli* pGAP-Ia-gapP-atoB/B::atoDAB::pnt in which the expression of the thiolase gene (atoB) was enhanced in the genome as well as enhanced by the plasmid, and in which the expression of the NAD(P)$^+$ transhydrogenase (AB-specific) gene (pnt) was enhanced.

Example 14

[pGAP-Ia-maeB-gapP-atoB/B::atoDAB::pnt Strain]: Preparation of *Escherichia coli* B Genome-Enhanced atoDAB and pntA Strain by Introduction of pGAP-Ia-maeB-gapP-atoB The B::atoDAB::pnt strain produced in Example 11 was transformed with the pGAP-Ia-maeB-gapP-atoB described in Example 9 above, to obtain an isopropyl alcohol-producing *Escherichia coli* pGAP-Ia-maeB-gapP-atoB/B::atoDAB::pnt strain in which the expression of the malate dehydrogenase gene (maeB) and the NAD(P)$^+$ transhydrogenase (AB-specific) gene (pnt) was enhanced, and in which the expression of the thiolase gene (atoB) was enhanced in the genome as well as enhanced by the plasmid.

Evaluation Experiment 1

Production of Isopropyl Alcohol by [pGAP-Iaaa/B Strain], [pGAP-Iaaa/B::pntA Strain], [pGAP-Ia-gapP-atoB/B::atoDAB Strain], [pGAP-Ia-maeB/B::atoDAB Strain], [pGAP-Ia-maeB-gapP-atoB/B::atoDAB Strain], [pGAP-Ia-maeB/B::atoDAB::pnt], [pGAP-Ia-gapP-atoB/B::atoDAB::pnt], and [pGAP-Ia-maeB-gapP-atoB/B::atoDAB::pnt Strain]

In the present evaluation experiment, isopropyl alcohol was produced using the production apparatus shown in FIG. 1 of the pamphlet of WO2009/008377. The culture tank used had a 3 L capacity, and the trap tank used had a 10 L capacity. The culture tank, the trap tank, the injection tube, the connection tube, and the discharge tube were all made of glass. Water as a trap liquid (trap water) in an amount of 9 L was injected into the trap tank. In addition, the culture tank was provided with a waste solution disposal tube to discharge a culture solution, of which the amount was increased due to flow addition of sugar and a neutralizer, to the outside of the culture tank as needed.

Mach of the pGAP-Iaaa/B strain described in the pamphlet of W2009/008377, the pGAP-Iaaa/B::pnt strain prepared in Example 2 above, the pGAP-Ia-gapP-atoB/B::atoDAB strain prepared in Example 6 above, the pGAP-Ia-maeB/B::atoDAB strain prepared in Example 8, the pGAP-Ia-maeB-gapP-atoB/B::atoDAB strain prepared in Example 10, the pGAP-Ia-maeB/B::atoDAB::pnt strain prepared in Example 12, the pGAP-Ia-gapP-atoB/B::atoDAB::pnt strain prepared in Example 13, and the pGAP-Ia-maeB-gapP-atoB/B::atoDAB::pnt strain prepared in Example 14 was inoculated, for preculturing, into a 500 mL capacity Erlenmeyer flask that contained 100 ML of an LB Broth, Miller culture solution (Difco 244620) containing 50 μm/mL of ampicillin, and was precultured overnight at a culture temperature of 30° C. while stirring at a rate of 120 rpm.

In addition, the pGAP-Iaaa/B strain described in the pamphlet of W2009/008377 is provided with only the thiolase activity in order to produce isopropyl alcohol, and enhancement of both the malate dehydrogenase activity and the NAD(P)$^+$ transhydrogenase (AB-specific) activity has not been carried out. Therefore, the pGAP-Iaaa/B strain does not read on the isopropyl alcohol-producing *Escherichia coli* of the present invention.

The preculture product (45 mL) obtained was transferred into a 3 L capacity culture tank (BMS-PI: a culture apparatus manufactured by ABLE Corporation) containing 855 g of a culture medium having the composition shown below, and was cultured. The cultivation was performed under atmospheric pressure, at an aeration rate of 0.9 L/min, a stirring speed of 550 rpm, a culture temperature of 30° C., and pH 7.0 (adjusted with an aqueous NH$_3$ solution). During the period from the start of the culture until 8 hours thereafter, a 45% wt/wt glucose aqueous solution was added at a flow rate of 7.5 g/L/hour. After that, the 45% wt/wt glucose aqueous solution was added at a flow rate of 20 g/L/hour. The bacterial cell culture solution was sampled a few times during the period from the start of the culture until 72 hours thereafter, and bacterial cells were removed by centrifugal operation. The amounts of isopropyl alcohol accumulated in the obtained culture supernatant and the trap water were measured by HPLC according to a usual method. The measurement values show the total value of the accumulation amounts in the culture solution and the trap water (9 L) after the culturing. The results are shown in FIG. 1 and Table 1. In addition, the production rates, the yields, and the amounts of isopropyl alcohol accumulated are all shown in FIG. 2.

The values in Table 1 are given in g/L. The symbols in FIG. 1 are defined as follows:

Black circle: pGAP-Ia-maeB-gapP-atoB:B::atoDAB::pnt strain;

Black square: pGAP-Ia-maeB-gapP-atoB/B::atoDAB strain;

White circle: pGAP-Ia-maeB/B::atoDAB strain;

White triangle: pGAP-Ia-gapP-atoB/B::atoDAB strain;

White square: pGAP-Iaaa/B::pnt strain;

×: pGAP-Iaaa/B strain;

White rhombus: pGAP-Ia-maeB/B::atoDAB::pnt strain; and

Black rhombus: pGAP-Ia-gapP-atoB/B::atoDAB::pnt strain.

<Composition of Culture Medium>

Corn steep liquor (manufactured by Nihon Shokuhin Kako Co., Ltd.): 20 g/L

Fe$_2$SO$_4$.7H$_2$O: 0.1 g/L

K$_2$HPO$_4$: 2 g/L

KH$_2$PO$_4$: 2 g/L

MgSO$_4$.7H$_2$O: 2 g/L (NH$_4$)$_2$ SO$_4$: 2 g/L

ADEKANOL LG126 (Asahi Denka Co. Ltd.): 0.1 g/L (Balance: water)

TABLE 1

| Time (hr) | pGAP-Iaaa/B strain | pGAP-Iaaa/B::pntA strain | pGAP-Ia-gapP-atoB/B::atoDAB strain | pGAP-Ia-maeB/B::atoDAB strain | pGAP-Ia-maeB-gapP-atoB/B::atoDAB strain | pGAP-Ia-maeB/B::atoDAB::pnt strain | pGAP-Ia-gapP-atoB/B::atoDAB::pnt strain | pGAP-Ia-maeB-gapP-atoB/B::atoDAB::pnt strain |
|---|---|---|---|---|---|---|---|---|
| 0 | 0.0 | 0.0 | 0.0 | 0.0 | 0.0 | 0.0 | 0.0 | 0.0 |
| 3 | 0.4 | 0.1 | 0.3 | 0.0 | 0.0 | 0.1 | 0.0 | 0.0 |
| 6 | 1.4 | 0.7 | 0.3 | 0.2 | 0.0 | 0.5 | 0.4 | 1.2 |
| 9 | 2.4 | 2.7 | 3.5 | 2.1 | 4.1 | 3.1 | 2.4 | 4.9 |
| 24 | 13.3 | 15.7 | 26.4 | 16.7 | 31.5 | 22.0 | 26.1 | 32.7 |
| 30 | 16.6 | 25.6 | 24.7 | 26.7 | 41.5 | 36.0 | 42.7 | 48.7 |
| 48 | 24.4 | 36.8 | 53.6 | 48.9 | 65.9 | 53.6 | 50.5 | 80.4 |
| 54 | 28.4 | 42.2 | 58.7 | 49.8 | 72.5 | 84.0 | 80.6 | 81.4 |
| 72 | 34.7 | 59.6 | 70.7 | 72.7 | 82.5 | 83.5 | 80.6 | 97.4 |

TABLE 2

| Name of strain | pGAP-Iaaa/B strain | pGAP-Iaaa/B::pntA strain | pGAP-Ia-gapP-atoB/B::atoDAB strain | pGAP-Ia-maeB/B::atoDAB strain | pGAP-Ia-maeB-gaP-atoB/B::atoDAB strain | pGAP-Ia-maeB/B::atoDAB::pnt strain | pGAP-Ia-gapP-atoB/B::atoDAB::pnt strain | pGAP-Ia-maeB-gapP-atoB/B::atoDAB::pnt strain |
|---|---|---|---|---|---|---|---|---|
| Production rate (g-IPA/L/hr) | 0.6 | 0.9 | 1.0 | 1.2 | 1.4 | 1.1 | 1.16 | 1.9 |
| Yield (mol-IPA/mol-glucose) % | 30.9 | 28.1 | 42.7 | 39.6 | 67.1 | 50.9 | 45.5 | 65.6 |
| Amount of accumulation (g-IPA/L) | 34.7 (72 hr) | 59.6 (72 hr) | 70.7 (72 hr) | 72.7 (72 hr) | 82.5 (72 hr) | 80.5 (72 hr) | 83.5 (72 hr) | 97.4 (72 hr) |

As shown in these results, the strain (pGAP-Iaaa/B::pntA strain) in which only the expression of the NAD(P)$^+$ transhydrogenase (AB-specific) gene (pnt) was enhanced in the conventional isopropyl alcohol-producing *Escherichia coli* (pGAP-Iaaa/B strain), the strain (pGAP-Ia-gapP-atoB/B::atoDAB strain) in which only the expression of the thiolase gene (atoB) was enhanced by both the introduction and the genomic enhancement in the conventional pGAP-Iaaa/B strain, and the strain (pGAP-Ia-maeB/B::atoDAB strain) in which only the expression of the malate dehydrogenase gene (maeB) was enhanced in the conventional pGAP-Iaaa/B strain all showed higher productivity than the conventional isopropyl alcohol-producing *Escherichia coli*, and the respective amounts of accumulation of isopropyl alcohol were approximately 1.7 times, approximately, 2.0 times, and approximately 2.1 times that of the conventional isopropyl alcohol-producing *Escherichia coli*, respectively. In the strain (pGAP-Ia-maeB/B::atoDAB strain) in which only the expression of the malate dehydrogenase gene (maeB) was enhanced, by-products such as acetone, formic acid, and acetic acid were reduced.

Furthermore, the strain (pGAP-Ia-maeB-gapP-atoB/B::atoDAB strain) in which both atoB and maeB are enhanced, the strain (pGAP-Ia-maeB/B::atoDAB::pnt) in which the expression of both maeB and pnt is enhanced, the strain (pGAP-Ia-gapP-atoB/B::atoDAB::pnt) in which atoB and pnt are enhanced, and the strain in which the expression of all of the three enzyme genes: atoB, maeB, and pnt is enhanced further improved productivity of isopropyl alcohol. The respective amounts of accumulation of isopropyl alcohol were approximately 2.4 times, approximately 2.3 times, approximately 2.4 times, and approximately 2.8 times that of the conventional isopropyl alcohol-producing *Escherichia coli*, respectively. Particularly, in the case in which the expression of the NAD(P)$^+$ transhydrogenase (AB-specific) (pnt), the thiolase gene (atoB), and the malate dehydrogenase gene (maeB) was simultaneously enhanced, the production rate was 3.4 times that of the pGAP-Iaaa/B strain, the yield was 2.1 times that of the pGAP-Iaaa/B strain, and the amount of accumulation of isopropyl alcohol was 2.8 times that of the pGAP-Iaaa/B strain, which are drastic improvements.

The disclosure of Japanese Patent Application No: 2010-052249 filed on Mar. 9, 2010 is incorporated herein by reference in its entirety.

All publications, patent applications, and technical standards mentioned in this specification are incorporated herein by reference to the same extent as if each individual publication, patent application, and technical standard were specifically and individually indicated to be incorporated by reference.

The invention claimed is:

1. An isopropyl alcohol-producing *Escherichia coli* comprises an isopropyl alcohol production system, comprising at least one enhanced enzyme activity selected from the group consisting of:
   an enhanced malate dehydrogenase activity and
   an enhanced NAD(P)$^+$ transhydrogenase (AB-specific) activity,
   wherein the enhanced enzyme activity represents that the enzyme activity in the isopropyl alcohol-producing *Escherichia coli* after enhancement are higher than those before the enhancement, and
   wherein the enhancement of enzyme activity results in the production of increased isopropyl alcohol.

2. The isopropyl alcohol-producing *Escherichia coli* according to claim 1, wherein the enhanced enzyme activity comprises the enhanced malate dehydrogenase activity.

3. The isopropyl alcohol-producing *Escherichia coli* according to claim 2, wherein the enhanced enzyme activity comprises the enhanced malate dehydrogenase activity and further comprises an enhanced thiolase activity.

4. The isopropyl alcohol-producing *Escherichia coli* according to claim 1, wherein the enhanced enzyme activity comprises the enhanced malate dehydrogenase activity and the enhanced NAD(P)$^+$ transhydrogenase (AB-specific) activity.

5. The isopropyl alcohol-producing *Escherichia coli* according to claim 4, wherein the enhanced enzyme activity comprises the enhanced malate dehydrogenase activity, the enhanced NAD(P)$^+$ transhydrogenase (AB-specific) activity, and further comprises an enhanced thiolase activity.

6. The isopropyl alcohol-producing *Escherichia coil* according to claim 1, wherein the enhanced enzyme activity is derived from at least one of enhancement by an enzyme gene introduced from outside the cell of the *Escherichia coli* or enhancement by enhanced expression of an enzyme gen the cell of the *Escherichia coli*.

7. The isopropyl alcohol-producing *Escherichia coli* according to claim 1, wherein the enhanced enzyme activity is derived from at least one of enhancement in the genome of a host *Escherichia coil* or enhancement by plasmid introduction.

8. The isopropyl alcohol-producing *Escherichia coli* according to claim 1, wherein the enhanced enzyme activity is derived from a gene derived from a bacterium of the genus *Escherichia* and encoding the enzyme or enzymes.

9. The isopropyl alcohol-producing *Escherichia coli* according to claim 1, wherein the isopropyl alcohol production system is constructed by genes of each of acetoacetate decarboxylase, isopropyl alcohol dehydrogenase, acetoacetyl-CoA transferase, and thiolase enzymes.

10. The isopropyl alcohol-producing *Escherichia coli* according to claim 1, wherein the isopropyl alcohol production system is constructed by enzyme genes of each of the acetoacetate decarboxylase, the isopropyl alcohol dehydrogenase, the acetoacetyl-CoA transferase, and the thiolase, and the respective genes of the enzymes are independently derived from at least one prokaryote selected from the group consisting of a bacterium of the genus *Clostridium*, a bacterium of the genus *Bacillus*, and a bacterium of the genus *Escherichia*.

11. The isopropyl alcohol-producing *Escherichia coli* according to claim 4, wherein the malate dehydrogenase activity, and the NAD(P)$^+$ transhydrogenase (AB-specific) activity are derived from genes that are derived from *Escherichia coli* and encode the respective enzymes.

12. The isopropyl alcohol-producing *Escherichia coli* according to claim 9, wherein the acetoacetate decarboxylase activity is derived from a gene that is derived from *Clostridium acetobutylicum* and encodes the enzyme; the isopropyl alcohol dehydrogenase activity is derived from a gene that is derived from *Clostridium beijerinckii* and encodes the enzyme; and the CoA transferase activity and the thiolase activity are derived from genes that are derived from *Escherichia coli* and encode the respective enzymes.

13. An isopropyl alcohol producing method comprising producing isopropyl alcohol from a plant-derived raw material using the isopropyl alcohol-producing *Escherichia coli* according to claim 1.

* * * * *